United States Patent [19]
Honna et al.

[11] 3,944,626
[45] Mar. 16, 1976

[54] PROCESS FOR PRODUCING ADAMANTANE COMPOUNDS

[76] Inventors: Kosaku Honna; Nobuaki Shimizu, both of Kammizumi, Sodegauro-cho, Kimitsu, Chiba; Konomu Kurisaki, Kmazuasayama, Ichihara, Chiba, all of Japan

[22] Filed: Apr. 16, 1974

[21] Appl. No.: 461,397

[30] Foreign Application Priority Data
Apr. 26, 1973 Japan.................................. 48-46635
July 30, 1973 Japan.................................. 48-84869

[52] U.S. Cl............................................. 260/666 M
[51] Int. Cl.$^2$............................................. C07C 5/24
[58] Field of Search .............................. 260/666 M

[56] References Cited
UNITED STATES PATENTS

| | | | |
|---|---|---|---|
| 3,803,253 | 4/1974 | Suld.................................. | 260/668 F |
| 3,418,387 | 12/1968 | Hala et al......................... | 260/666 M |
| 3,637,876 | 1/1972 | Bagry et al...................... | 260/666 M |
| 3,671,599 | 6/1972 | Moore.............................. | 260/666 M |

*Primary Examiner*—Delbert E. Gantz
*Assistant Examiner*—C. E. Spresser
*Attorney, Agent, or Firm*—McGlew and Tuttle

[57] ABSTRACT

Adamantane compound is obtained by isomerizing a tricyclic saturated hydrocarbon having 10 to 14 carbon atoms in the presence of an X- or Y-type zeolite catalyst subjected to ion exchange with one or two kinds of metal ions selected from the group consisting of ions of rare earth metals, calcium and magnesium. The preferred catalyst is a catalyst which is further loaded with 1 to 4 kinds of metals selected from the group consisting of germanium, platinum, rhenium, nickel, cobalt, copper, iron ruthenium and rhodium. This isomerization reaction is preferably carried out in the presence of hydrogen gas.

12 Claims, No Drawings

PROCESS FOR PRODUCING ADAMANTANE COMPOUNDS

DETAILED DESCRIPTION OF THE INVENTION

The present invention relates to a method of producing adamantane compounds.

Adamantane is known to be contained in petroleum naturally. Its unique chemical structure has attracted attention and a lot of investigations have been made with regard to its synthesis method, usage, etc.

Recently, the use of adamantane compounds as medicine, lubricant, etc. has been developed and industrially advantageous production process is expected to appear.

Generally, adamantane compounds are obtained by isomerization reaction of tricyclic hydrocarbon and aluminium halide such as $AlCl_3$, $AlBr_3$, etc. has been conventionally used as catalyst of this reaction in most cases. However, this type of catalyst possesses various defects, for example, it must be used in large quantities (against raw material), it is difficult to be regenerated because complex is formed combined with heavy elements during the course of reaction, the reaction equipment is easily corroded, it needs to add fresh catalyst for the consumed amount in order to carry out the reaction continuously.

On the other hand, solid catalyst such as $Pt-Al_2O_3-Cl$, $Al_2O_3$ treated with sulfuric acid, etc. has been also used as another type of catalyst. It has an advantage of being regenerated easily. However, it shows very low activity and its catalytic life is short.

Such being the case, the purpose of this invention lies in the description of a method of producing adamantane compounds under advantageous conditions from industrial viewpoint with high active solid catalyst. That is, this invention is characterized in that, in the process of producing hydrocarbon with adamantane structure by isomerizing tricyclic saturated hydrocarbon having more than 10 carbon atoms, zeolite subjected to ion exchange with one or more kinds of metal ions selected from the group composed of ions of rare earth metals and ions of alkali earth metals is used as a catalyst.

Further, this invention intends to employ another catalyst, that is, zeolite catalyst subjected to ion exchange with one or more kinds of metal ions selected from the group composed of ions of rare earth metals and ions of alkali earth metals and further being carried with germanium and/or one or more kinds of transition elements which have an ability of dehydrogenation-hydrogenation reaction also can be used. Transition elements which may be preferably used for this invention are as follows; platinum, rhenium, nickel, cobalt, copper, iron, ruthenium, rhodium and the like.

The catalyst used in the process of this invention is obtained as follows: zeolite is treated with rare earth metals such as La, Ce, Nd, Yb, Y, etc. and/or alkali earth metals such as Ca, Mg, etc. in the form of, for instance, metallic salt solution, dried and calcined.

Subsequently, if necessary, the catalyst is further carried with germanium and/or one or more kinds of transition elements. These elements may be added to zeolite before calcing. The amount of metal (i.e. transion element and germanium) in the catalyst is from 0.1 to 20%(wt.), preferably from 0.1 to 10%(wt.) and more preferably from 0.1 to 5%(wt.). In producing the catalyst, rare earth metals and/or alkali earth metals are not carried with zeolite, should be incorporated to it in the form of one subjected to ion exchange with cation site (for example, $Na^+$, $K^+$, $NH_4^+$, etc.) in Y-type or X-type zeolite. Ion exchange rate is from 5 to 100%, preferably from 30 to 100% and more preferably from 50-100%. Practically, it is preferred to be higher than 50% when Na—Y, K—Y, etc. are used and to be higher than 10% when $NH_4$—Y is used. Zeolite is preferred to be Y-type or X-type.

At the time of combining Ge and/or transition element with zeolite, the method is not limited to ion exchange method but any suitable method such as impregnation method can be adopted. The addition of Ge and/or transition element to the catalyst brings about more favourable result, especially coexistence of two kinds of metals causes synergistic effect.

The material used for isomerization reaction is tricyclic saturated hydrocarbon having more than 10 carbon atoms, preferably the one in which strain of carbon-to-carbon combination is relatively large. Raw material that may be used for this invention is enumerated in Table 1.

Table 1

| Number of Carbon | Tricyclic Saturated Hydrocarbon | |
| --- | --- | --- |
| 10 | tetrahydrodicyclopentadiene |  |
| 12 | perhydroacenaphthene |  |
| 13 | perhydrofluolene |  |
| 13 | perhydrophenarene |  |
| 13 | 1,2-cyclopentanoperhydro-naphthalin |  |
| 14 | perhydroanthracene |  |
| 14 | perhydrophenanthrene |  |
| 14 | 9-methylperhydro-anthracene |  |

These kinds of tricyclic saturated hydrocarbon are easily obtained by known method, for instance, by hydrogenation of the corresponding hydrocarbon under the existence of catalyst (for example, Raney nickel, platinum, etc.).

Isomerization reaction is carried out under the existence of catalyst at a temperature of about 50°–500°C, preferably 100°–500°C, more preferably 150°–300°C, under atmospheric or increased pressure of 1–150 $kg/cm^2$, preferably 5–150 $kg/cm^2$ and more preferably 10–100 $kg/cm^2$. Reaction can be done by either flow system or batch system. In the case of batch system, the used amount of catalyst is about 0.2–2.0 (wt. of catalyst/wt. of raw material) and the contact time is about 1–50 hours. When reaction pressure must be decreased, pretreatment of catalyst under coexistence of $H_2$ and HCl is effective. Presence of HCl gas and/or $H_2$ gas improves the reaction yield and life of the catalyst, especially presence of both gases gives a synergistic effect. In the case, molar fraction of HCl is adjusted to 0.01–1.00, preferably 0.01–0.9, more preferably 0.05–0.9. Addition of brominated hydrocarbon such as bromo adamantane (AdBr) is also effective. Higher pressure of $H_2$ gas gives favourable results in yield of final product and life of the catalyst.

ducing hydrogen gas to 6 atm. The mixture was heated to 250°C and the reaction was carried out for 5 hr with stirring. After the reaction was completed, the content was dissolved in n-hexane and catalyst was removed by filtration. The resulted colorless and transparent solution was concentrated by distillation and adamantane with more than 99% of purity was precipitated as needless by standing the concentrate for several hours at ordinary temperature. Under the above conditions, conversion rate of TMN, selectivity of adamantane (AdH) formation and yield of AdH formation were shown in Table 2.

Table 2

| Conc. of $La^{3+}$ (mol/l) | Ion exchange rate (%) [1] | Conversion rate of TMN (%) [2] | Selectivity of AdH (%) [3] | Yield of AdH (%) [4] |
|---|---|---|---|---|
| 0.01 | 28.4 | 20.0 | 51.0 | 10.2 |
| 0.07 | 49.8 | 18.8 | 50.0 | 9.4 |
| 0.21 | 54.3 | 27.6 | 46.4 | 12.8 |
| 0.21 | 58.7[5] | 41.9 | 42.7 | 17.9 |

Note:
1) Ion exchange rate
$$= 1 - \frac{\text{Contents of Na}^+ \text{ in Zeolite after ion exchange}}{\text{contents of Na}^+ \text{ in Zeolite SK-40}} \times 100$$
2) Conversion rate of TMN
$$= 1 - \frac{\text{the number of moles of TMN after reaction}}{\text{the number of moles of TMN before reaction}} \times 100$$
3) Selectivity of AdH
$$= \frac{\text{moles of AdH formed}}{(\text{moles of TMN before reaction}) - (\text{moles of TMN after reaction})} \times 100$$
4) Yield of AdH
= (conversion rate of TMN) × (selectivity of AdH)
5) Ion exchanged at 200°C.

The process of this invention is characterized in a small amount of catalyst to be used, high catalytic activity and high reaction yield. Moreover, the catalyst can be easily regenerated. It is one of the merits of this invention that the purification of the product is easy and the equipment is hardly corroded.

The catalyst used in this invention is regenerated by deairing the used catalyst at a temperature of 150° to 250°C under a vacuum. For the complete regeneration, it is necessary to calcine at a temperature of 350° to 550°C under the existence of air.

The present invention is further illustrated in the following examples.

EXAMPLE 1

Ten grams of Zeolite (Y-type) consisting of $SiO_2$ 63.5 wt.%, $Al_2O_3$ 23.5 wt.% and $Na_2O$ 13.0 wt.%, which is sold under trademark SK-40 by Union Carbide, U.S.A., were added to 1 liter of $La^{3+}$ aqueous solution prepared by dissolving various amounts of $La(NO_3)_3 \cdot 6H_2O$ into pure water and the mixture was stirred for 15 hr at 80°C. Subsequently, the mixture was filtered at ordinary temperature and resulted cake-like product was washed thoroughly with pure water and then was dried at 100°C. Finally it was calcined at a temperature of 475°C for 3 hr in a stream of helium and thus powdered catalysts having various ion exchange capacities were obtained.

Various kinds of catalysts (2 g) prepared by above mentioned method and 4 g of endo-trimethylene norbornane (TMN) of over 95% purity which was prepared by hydrogenation of di-cyclopentadiene were placed in a stainless steel autoclave having a content of 100 ml, and the pressure in the autoclave was reduced and degassed to vacuum. Then gaseous HCl was introduced to 1 atm. of absolute pressure followed by intro-

COMPARATIVE EXAMPLE 1

The reaction was carried out in the same manner as described in Example 1 except that Zeolite SK-40 was calcined without ion exchange with $La^{3+}$. Under the above condition, conversion rate of TMN, selectivity of AdH and yield of AdH were 9.8%, 42.8% and 4.2% respectively. From this result, effect of ion exchange by $La^{3+}$ was unambiguously confirmed.

COMPARATIVE EXAMPLE 2

Zeolite SK-40 (9.5 g) was added to 100 ml of aqueous solution of $La(NO_3)_3$ (0.03 N) and the mixture was stirred for 30 min at ordinary temperature and then water was removed in vacuo. Subsequently resulted cake was dried at 110°C and finally was calcined at 475°C for 3 hr in a stream of helium. Thus powdered Zeolite catalyst containing 5 wt.% of $La_2O_3$ was obtained.

When the reaction was conducted using this catalyst, conversion rate of TMN was 1.6%. This example clearly indicated that $La^{3+}$ must be added to the catalyst by ion exchange with $Na^+$.

EXAMPLE 2

The reaction was carried out in the same manner as described in Example 1 except that ion exchange of catalyst was carried out by various rare earth elements in place of $La^{3+}$. Results of experiments were summarized in Table 3.

Table 3

| Rare earth element used | Ion exchange rate (%) | Conversion rate of TMN (%) | Selectivity of AdH (%) | Yield of AdH (%) |
|---|---|---|---|---|
| Ce | 52.6 | 22.7 | 46.7 | 10.6 |

Table 3-continued

| Rare earth element used | Ion exchange rate (%) | Conversion rate of TMN (%) | Selectivity of AdH (%) | Yield of AdH (%) |
|---|---|---|---|---|
| Ce | 53.4 | 27.7 | 40.8 | 11.3 |
| Nd | 6.2 | 27.4 | 42.7 | 11.7 |
| Nd | 62.1 | 39.2 | 42.6 | 16.7 |
| Yb | 54.7 | 30.8 | 38.9 | 12.0 |
| Y | 53.4 | 23.0 | 43.5 | 10.0 |

EXAMPLE 3

Ten grams of Zeolite (Y-type) consisting of $SiO_2$ 65.0 wt.%, $Al_2O_3$ 23.0 wt.%, $(NH_4)_2O$ 9.6 wt.% and $Na_2O$ 2.4 wt.%, which is sold under trademark SK-41 by Union Carbide, were added to 1 liter of aqueous solution of 0.02 N $Ca(NO_3)_2.4H_2O$ and the mixture was stirred for 10 hr at 80°C. Subsequently the mixture was filtered at ordinary temperature and resulted cake-like substance was washed with 1 liter of pure water. Furthermore the above procedures were repeated twice.

The cake-like substance was then placed in 1 liter of 0.02 N $La(NO_3)_3.6H_2O$ solution and the mixture was stirred for 10 hr at 80°C. The mixture was filtered at ordinary temperature and was washed with 1 liter of pure water. The whole procedures described were repeated three times.

The cake-like product obtained by the above mentioned procedures was dried at 100°C and then placed in a porcelain plate in order to calcine by the following procedures; 1 hr at 250°C raising from room temperature, 1 hr at 350°C and finally 3 hr at 475°C. All the calcining procedures were carried out in a stream of He (50 cc/min). By these procedures, powdered catalyst was obtained, in which 13% of $NH_4^+$ and $Na^+$ in the starting material, Zeolite SK-41, and 2.4% of them were ion-exchanged by $La^{3+}$ and $Ca^{2+}$ respectively.

Adamantane synthesis using this catalyst was carried out in the same manner as described in Example 1 and it was found that conversion rate of TMN, selectivity of AdH and yield of AdH were 23.2%, 46.0% and 10.7% respectively.

EXAMPLE 4

Ten grams of Zeolite catalyst obtained by the same manner as described in Example 3 was mixed with prescribed amounts of Pt-solution prepared by dissolving 0.1 wt.% of $PtCl_2$ in ammonia water and of Re-solution prepared by dissolving 0.1 wt.% of $NH_4ReO_4$ in pure water at ordinary temperature and then the mixture was impregnated and evaporated to dryness using a rotary evaporator. Subsequently the cake obtained was placed in a porcelain plate in order to calcine in the following procedures; in a stream of He (50 cc/min), temperature was raised to 250°C from room temperature and kept at 250°C for 1 hr, then at 350°C for 1 hr and finally at 475°C for 3 hr. According to the above procedures, powdered catalyst was obtained, which contained total amounts of 2.5 wt.% of Pt and Re in various proportions of these two elements. Adamantane synthesis using these catalysts was carried out in the same manner as described in Example 1 and results were shown in Table 4.

Table 4

| Amount of Pt-soln. (ml) | Amount of Re-soln. (ml) | Ratio* of Re | Conversion rate of TMN(%) | Selectivity of AdH (%) | Yield of AdH(%) |
|---|---|---|---|---|---|
| 343 | 0 | 0 | 41.1 | 35.0 | 14.4 |
| 257 | 91 | 0.25 | 77.2 | 34.2 | 26.4 |
| 206 | 146 | 0.40 | 73.2 | 33.9 | 24.8 |
| 172 | 182 | 0.50 | 28.2 | 52.0 | 14.7 |
| 86 | 273 | 0.75 | 37.9 | 48.0 | 18.2 |
| 0 | 364 | 1.00 | 24.5 | 49.0 | 12.0 |

*Ratio of Re
$$= \frac{\text{numbers of Re atoms in the catalyst}}{\{\text{numbers of Re atoms in the catalyst}\} + \{\text{numbers of Pt atoms in the catalyst}\}}$$

COMPARATIVE EXAMPLE 3

Synthesis of adamantane was carried out using $Al_2O_3$ catalyst containing total amounts of 1.0 wt.% of Pt and Re at ratio of Re in 0.25, in the same manner as described in Example 4, Conversion rate of TMN was 4.1%.

EXAMPLE 5

A catalyst (2 g) which was prepared from Zeolite SK-41 by ion-exchange with $Ca^{2+}$ at 2.4% and with $La^{3+}$ at 13% and further by being included total amounts of 1.0 wt.% of Pt and Re at ratio of Re in 0.25, and 4 g of TMN were placed in a stainless steel autoclave having a content of 100 ml, and the pressure of the autoclave was reduced and degassed. Subsequently various kinds of gases were introduced to prescribed pressure and the reaction was proceeeded with stirring at 250°C for 5 hr. Results of experiments were shown in Table 5.

Table 5

| Total Pressure (atm) | HCl Pressure (atm) | $H_2$ Pressure (atm) | He Pressure (atm) | $N_2$ Pressure (atm) | Conversion rate of TMN (%) | Selectivity of AdH (%) | Yield of AdH (%) |
|---|---|---|---|---|---|---|---|
| 1 | — | — | — | 1 | 16.9 | 40.2 | 6.8 |
| 7 | — | — | 7 | — | 12.9 | 41.1 | 5.3 |
| 16 | — | — | 16 | — | 11.7 | 42.7 | 5.0 |
| 16 | 16 | — | — | — | 5.2 | 32.7 | 1.7 |
| 16 | 11 | 5 | — | — | 29.8 | 47.3 | 14.1 |
| 16 | 6 | 10 | — | — | 84.9 | 34.9 | 29.6 |
| 16 | 1 | 15 | — | — | 93.1 | 23.7 | 22.1 |
| 16 | — | 16 | — | — | 79.5 | 10.1 | 8.0 |

EXAMPLE 6

The same catalyst employed in Example 5 was pretreated with heating at 60°C for 1 hr under the toral pressure of 16 atm., which comprised of partial pressure of $H_2$ at 15 atm. and of HCl at 1 atm. The catalyst thus obtained (2 g) was placed in an autoclave of a content of 100 ml together with 4 g of TMN. After evacuation and degassing, hydrogen gas was intoduced to absolute pressure of 1 atm. and the reaction was proceeded at 250°C for 5 hr. Conversion rate of TMN, selectivity of AdH and yield of AdH were 51.6%, 41.1% and 21.1% respectively. However, crystallines of AdH obtained showed a slight coloration.

EXAMPLE 7

A catalyst (2 g), which was prepared from Zeolite SK-41 by ion exchange with $Ca^{2+}$ at 10.3% and further by being included 0.5 wt.% of Pt, and 4 g of TMN were placed in an autoclave having a content of 100 ml. After evacuation and degassing, HCl gas and hydrogen gas were introduced to 1 atm. and 16 atm, respectively and the reaction was proceeded at 250°C for 5 hr while agitating. Conversion rate of TMN, selectivity of AdH and yield of AdH were 94.0%, 18.0% and 16.9% respectively.

EXAMPLE 8

The same experiment at described in Example 7 was carried out except that Mg was employed in place of Ca. Conversion rate of TMN, selectivity of AdH and yield of AdH were 96%, 19% and 18% respectively.

EXAMPLE 9

The catalyst used in the experiment indicated in 2th line from the bottom of Table 5 in Example 5 (partial pressure of HCl at 1 atm. and that of $H_2$ at 15 atom.) was dried and then calcined in a stream of air for 1 hr at 250°C, 1 hr at 350°C and finally for 3 hr at 500°C. The regenerated catalyst thus obtained (1.65 g) was used for synthesis of adamantane. Conversion rate of TMN was 67.9% which corresponded to 41.2% per g of the catalyst. (cf. in Example 5, conversion rate of TMN was 46.6% per g of catalyst.)

Furthermore the catalyst was again regenerated catalyst was also employed for the reaction. Using 1 g of the catalyst, conversion rate of TMN was found to be 42.0% which corresponded to 42.0% per g of the catalyst. From these examples, it was confirmed that the catalyst could be regenerated and reused. In addition, catalytic activity was directly proportional to the amounts of the catalyst under the conditions tested.

EXAMPLE 10

The same experiment as described in 2th line from the bottom in Table 5 of Example 5 was carried out except that perhydroacenaphthene prepared by hydrogenation of acenaphthene was used in place of TMN. Conversion rate of perhydroacenaphthene was 75.4%, and 1,3-dimethyladamantane and 1-ethyladamantane were obtained at 33.0% and 47.1% of selectivity and at 24.9% and 35.0% of yield respectively. Moreover, when amounts of catalyst was increased from 2 g to 4 g, conversion rate of perhydroacenaphthene was 85.6%, and 1,3-dimethyladamantane and 1-ethyladamantane were obtained at 45.2% and 6.6% of selectivity and at 38.7% and 5.7% of yield respectively.

EXAMPLE 11

The same experiment as described in 2th line from the bottom in Table 5 of Example 5 was carried out except that perhydrofluorene prepared by hydrogenation of fluorene was used in place of TMN and the reaction temperature was 300°C. Conversion rate of perhydrofluorene, selectivity and yield of 1,3,5-trimethyladamantane were 51.7%, 22.8% and 11.8%.

EXAMPLE 12

To 1 liter of 0.02N $Ca(NO_3)_2.4H_2O$ solution, 10 g of Y-type zeolite (produced by Union Carbide Co., Ltd., SK-41) possessing the composition of $SiO_2$ 65.0 wt.%, $Al_2O_3$ 23.0 wt.%, $(NH_4)_2O$ 9.6 wt.% and $Na_2O$ 2.4 wt.% was added. The mixture was agitated at 80°C for 10 hours and filtered at a room temperature. Thus obtained cake-like substance was washed with 1 liter of pure water. This procedure was repeated twice.

Then, to said cake-like substance, 1 liter of 0.02N $La(NO_3)_2.6H_2O$ solution was added. The mixture was agitated at 80°C for 10 hours, filtered at a room temperature and washed with 1 liter of pure water. This procedure was repeated three times.

The cake-like substance obtained by aforementioned procedure was dried at 100°C to produce La, Ca-Y-type catalyst. Ni solution (300 cc) containing 7.66 g of $Ni(NO_3)_2.6H_2O$ was poured to this catalyst (50 g) and they were fully mixed. Subsequently, the mixture was impregnated, evaporated and dried with rotary evaporator. Obtained powder was placed in ceramic board and heated in the current of He 50 cc/min, then calcined for 1 hour at 250°C, for 1 hour at 350°C and for 3 hours at 475°C. In the last place, it was treated for 2 hours at 475°C in the mixed current of He and $H_2$. Thus obtained catalyst is Ni-carried La, Ca-Y-type zeolite catalyst containing 3 wt.% as Ni.

Two grams of this catalyst and 4 g of endotrimethylene-norbornane (TMN) which was obtained by hydrogenation of dicyclopentadiene were placed in a stainless autoclave with the capacity of 100 cc. The pressure in the autoclave was reduced and deaired to vacuum. Then HCl gas was introduced to reach 1 atm. of absolute pressure and further $H_2$ gas was introduced to reach 15 atom. The mixture was heated to 250°C and subjected to reaction for 2.5 hours.

After the termination of reaction, the reaction mixture was cooled, dissolved in n-hexane and filtered to exclude catalyst.

Obtaiined colorless transparent solution was condensed by distillation and left for a few hours at a room temperature, then needle-shaped crystal of adamantane (AdH) with more than 99% of purity was separated. TMN conversion ratio, AdH selectivity and AdH yield were respectively 49.6%, 46.3% and 23.0%.

On the other hand, the same reaction was done except that La, Ca-Y-type zeolite catalyst not containing Ni was used. In this reaction, TMN conversion ratio, AdH selectivity and AdH yield were respectively 43.4%, 41.2% and 17.9%.

EXAMPLE 13

To 50 g of La, Ca-Y-type zeolite catalyst, which was previously manufactured by the same way described in Example 12, 300 cc of Co solution containing 7.63 g of $Co(NO_3)_2.6H_2O$ was added. They were fully mixed and then treated in the same way as Example 12. Thus a catalyst containing 3 wt.% as Co was obtained.

As the result of the same reaction as Example 12 with this catalyst, TMN conversion ratio, AdH selectivity and AdH yield were respectively 54.7%, 47.5% and 26.0%.

EXAMPLE 14

To 50 g of La, Ca-Y-type zeolite catalyst, which was previously produced by the same way as Example 12, Ni solution (containing $Ni(NO_3)_2.6H_2O$), Pt solution (containing $H_2PtCl_6$) and Re solution (containing $NH_4ReO_4$) were poured and they were fully mixed. Treating the mixture in the same way as Example 12, a catalyst containing 1 wt.% as Ni, 0.75 wt.% as Pt and 0.25 wt.% Re (Re atomic ratio 0.25) was obtained.

As the result of the same reaction as Example 12 with this catalyst, TMN conversion ratio, AdH selectivity and AdH yield were respectively 66.2%, 44.4% and 29.4%.

EXAMPLE 15

To 50 g of La, Ca-Y-type zeolite catalyst, which was previously produced by the same way as Example 12, 300 cc of Ni solution containing 7.74 g of $Ni(NO_3)_2 \cdot 6H_2O$, 1038 cc of Pt solution ($H_2PtCl_6$, $1.930 \times 10^{-3}$ mol/l) and 187 cc of Re solution ($NH_4ReO_4$, $3.727 \times 10^{-3}$ mol/l) were poured and they were fully mixed.

Treating the mixture in the same way as Example 12, a catalyst containing 3 wt.% as Ni, 0.75 wt.% as Pt and 0.25 wt.% as Re (Re atomic ratio 0.25) was obtained.

As the result of the same reaction as Example 12 with this catalyst, TMN conversion ratio, AdH selectivity and AdH yield were respectively 69.0%, 43.0% and 30.0%.

EXAMPLE 16

To 50 g of La, Ca-Y-type zeolite catalyst, which was previously manufactured by the same way as Example 12, 300 cc of Co solution containing 7.71 g of $Co(NO_3)_2 \cdot 6H_2O$, 1038 cc of Pt solution (the same one as that used in Example 15) and 187 cc of Re solution (the same one as that used in Example 15) were added and they were fully mixed.

Treating the mixture in the same way as Example 12, a catalyst containing 3 wt.% as Co, 0.75 wt.% as Pt and 0.25 wt.% as Re (Re atomic ratio 0.25) was obtained.

As the result of the same reaction as Example 12 with this catalyst, TMN conversion ratio, AdH selectivity and AdH yield were respectively 91.5%, 33.8% and 30.9%.

EXAMPLE 17

The same reaction as Example 12 was done except that 4 g of perhydroacenaphtene obtained by hydrogenation of acenaphten was used instead of 4 g of endo-trimethylenenorbornane used in Example 12 and the same catalyst as that used in Example 14 was used. As the result, conversion ratio of perhydroacenaphten was 39.1%, selectivity of 1,3-dimethyladamantane was 28.4%, selectivity of 1-ethyladamantane was 52.4% and production ratio of the decomposed substances was 19.2%.

EXAMPLE 18

The same reaction as Example 17 was done except that the same catalyst as that used in Example 16 was used. As the result, conversion ratio of perhydroacenaphten was 17.5%, selectivity of 1,3-dimethyladamantane was 33.1%, selectivity of 1-ethyladamantane was 66.9% and production ratio of the decomposed substances was 0%.

EXAMPLE 19

Ten grams of Zeolite (Y-type), SK-41, consisting of $SiO_2$ 65.0 wt.%, $Al_2O_3$ 23.0wt.%, $(NH_4)_2O$ 9.6 wt.% and $Na_2O$ 2.4 wt.% were added to 1 liter of an aqueous solution of 0.02 N $Ca(NO_3)_2 \cdot 4H_2O$ and the mixture was stirred for 10 hr at 80°C. Subsequently the mixture was filtered at ordinary temperature and resulted cake-like substance was washed with 1 liter of pure water. Moreover the above procedures were repeated twice.

The cake-like substance was then placed in 1 liter of an aqueous solution of 0.02 N $La(NO_3)_3 \cdot 6H_2O$ and the mixture was stirred for 10 hr at 80°C. The mixture was filtered at ordinary temperature and was washed with 1 liter of pure water. The whole procedures described were repeated three times.

The cake-like substance obtained by the above procedures was dried at 100°C and thus La, Ca-Y-type catalyst was obtained.

The aqueous Cu-solution (300 ml) containing 1.587 g of $Cu(CH_3COO)_2 \cdot H_2O$ was poured on 50 g of the above catalyst and mixed thoroughly. Subsequently, the mixture was impregnated and evaporated to dryness using a rotary evaporator. The obtained powder was placed in a porcelain plate in order to calcine in the following procedures; in a stream of He (50 cc/min), temperature was raised to 250°C from room temperature and kept to 250°C for 1 hr, then at 350°C for 1 hr and finally at 475°C for 3 hr. Furthermore, the powder was calcined at 475°C for 2 hr in a stream of Re—$H_2$ mixture. The catalyst obtained was a Cu-carrying La, Ca-Y-type Zeolite catalyst containing 1 wt.% of copper as Cu.

The catalyst thus obtained (2 g) and 4 g of TMN obtained by hydrogenation of dicyclopentadiene were placed in a stainless steel autoclave having a content of 100 ml, and it was evacuated and degassed. Then gaseous HCl was introduced to absolute pressure of 1 atm. and further $H_2$ gas was introduced to 15 atm. and the reaction was proceeded at 250°C for 2.5 hr.

After the reaction was completed, the system was cooled and the content was dissolved in n-hexane and catalyst was removed by filtration. The resulted colorless transparent solution was concentrated and adamantane (AdH) of over 99% pure was precipitated as needles crystal by standing the concentrate for several hours at ordinary temperature.

Under the above conditions, conversion rate of TMN, selectivity of AdH and yield of AdH were 44.8%, 45.1% and 20.2% respectively.

EXAMPLE 20

Synthesis of AdH was carried out in the same manner as described in Example 19 except that La, Ca-Y-type Zeolite catalyst carrying 3 wt.% of Fe was used as the catalyst. Conversion rate of TMN, selectivity of AdH and yield of AdH were found to be 47.8%, 46.0% and 22.0%.

EXAMPLE 21

One hundred grams of La, Ca-Y-type Zeolite prepared in the manner described in Example 19 were mixed with 300 ml of Ni-solution containing 7.74 g of $Ni(NO_3)_2 \cdot 6H_2O$, 2076 ml of Pt-solution containing $1.930 \times 10^{-3}$ mol of $H_2PtCl_6$ per liter and 374 ml of Re-solution containing $3.727 \times 10^{-3}$ mol of $NH_4ReO_4$ per liter. The mixture was evaporated to dryness and then 100 ml of tetrachloromethane containing 4.62 g of $GeCl_4$ were added. Then the mixture was evaporated to dryness again.

The mixture was subsequently processed as described in Example 19 and the La, Ca-Y-type Zeolite catalyst containing of 1.5 wt.% of Ge, 1.5 wt.% of Ni, 0.75 wt.% of Pt and 0.25 wt.% of Re was obtained.

The above catalyst (50 ml) was packed in a flow-type stainless steel reaction tube (25 mm in inner diameter and 500 mm in length) and was calcined for 2 hr. at 250°–400°C in a stream of air. After replacement with $N_2$ gas, it was calcined further for 2 hr. at 200°–450°C at ordinary pressure in a stream of $H_2$ gas.

Subsequently the reaction was proceeded continuously at 195°C under 21 atm. of gauge pressure by supplying TMN at the rate of 10 ml/min. and $H_2$ gas at the rate of 6.48 times the molar quantity of TMN from the top of the tube-type reaction vessel.

Colorless and transparent reaction mixtures which had passed through the layer of catalyst were subjected to analyses by gas chromatography or to separation by crystallization. From these analytical procedures, conversion rate of TMN, selectivity of AdH and yield of AdH were found to be 43.7%, 32.8% and 14.3% respectively.

EXAMPLE 22

Synthesis of AdH was carried out in the same manner as described in Example 21 except that La, Ca-Y-type Zeolite catalyst containing 3 wt.% of Ni, 0.75 wt.% of Pt and 0.25 wt.% of Re was employed. As the result, conversion rate of TMN, selectivity of AdH and yield of AdH were 36.6%, 27.9% and 10.2% respectively.

EXAMPLE 23

The reaction was carried out in the same manner as described in Example 21 except that reaction pressure was 1 atm. of absolute pressure and $H_2$—HCl mixture gas consisting of 0.189 molar fraction of HCl was used in place of $H_2$ gas. Conversion rate of TMN, selectivity of AdH, and yield of AdH were found to be 39.5%, 40.8% and 16.1% respectively.

EXAMPLE 24

Synthesis of AdH was carried out in the same manner as described in Example 23 except that La, Ca-Y-type Zeolite catalyst containing 3 wt.% of Co, 0.75 wt.% of Pt and 0.25 wt.% of Re was employed and the reaction pressure was 1 atm. of absolute pressure and $H_2$—HCl mixture gas consisting of 0.063 molar fraction of HCl was used in place of $H_2$ gas. As the result, conversion rate of TMN was 47.2%, selectivity of AdH was 34.7% and yield of AdH was 16.4%.

EXAMPLE 25

Synthesis of AdH was carried out in the same manner as described in Example 24 except that $H_2$—HCl mixture gas consisting of 0.867 molar fraction of $H_2$ and 0.133 molar fraction of HCl was used. Conversion rate of TMN was 43.6%, selectivity of AdH was 37.1% and yield of AdH was 16.2%.

EXAMPLE 26

Synthesis of AdH was carried out in the same manner as described in Example 24 except that $H_2$—HCl mixture gas consisting of 0.811 molar fraction of $H_2$ and 0.189 molar fraction of HCl was used. Conversion rate of TMN was 40.5%, selectivity of AdH was 39.8% and yield of AdH was 16.1%.

EXAMPLE 27

The reaction was carried out in the same manner as described in Example 23 except that La, Ca-Y-type Zeolite catalyst containing 3 wt.% of Fe, 0.75 wt.% of Pt and 0.25 wt.% of Re was employed and $H_2$—HCl mixture gas consisting of 0.063 molar fraction of HCl was used. As the result, conversion rate of TMN was 49.5%, selectivity of AdH was 31.1% and yield of AdH was 15.4%.

EXAMPLE 28

The reaction was carried out in the same manner as described in Example 21 except that La, Ca-Y-type Zeolite catalyst containing 1.5 wt.% of Ge, 1.5 wt.% of Co, 0.75 wt.% of Pt and 0.25 wt.% of Re was employed.

Conversion rate of TMN, selectivity of AdH and yield of AdH were found to be 47.5%, 34.6% and 16.4% respectively.

On the other hand, the reaction was carried out in the same manner except that La, Ca-Y-type Zeolite catalyst containing 3 wt.% of Co, 0.75 wt.% of Pt and 0.25 wt.% of Re was employed. As the result, conversion rate of TMN, selectivity of AdH and yield of AdH were 40.2%, 29.9% and 12.0% respectively.

EXAMPLE 29

As described in Example 19, $GeCl_4$ was added to La, Ca-Y-type Zeolite prepared in the same manner as described in Example 21 and then the mixture was processed. Thus, the catalyst containing 1 wt.% of Ge was obtained.

The reaction was carried out in the same manner as described in Example 21 using this catalyst. Conversion rate of TMN, selectivity of AdH and yield of AdH were found to be 26.8%, 25.4% and 6.8% respectively.

On the other hand, the reaction was carried out in the same manner except that La, Ca-Y-type Zeolite catalyst which is not contained with Ge was employed as catalyst. Conversion rate of TMN, selectivity of AdH and yield of AdH wre 24.2%, 23.6% and 5.8% respectively.

EXAMPLE 30

To 50 g of La, Ca-Y-type Zeolite powder, which was prepared in the manner as described in Example 3, 54.9 ml of Ru-solution containing 0.0549 g (i.e. 1 g/l) of $RuCl_3.H_2O$ (Ru ion $4.437 \times 10^{-6}$ mol/ml) was poured and they were fully mixed at ordinary temperature. Subsequently, the mixture was impregnated, evaporated and dried with rotary evaporator.

Obtained powder was placed in a ceramic board and heated in the current of He 50 cc/min., then calcined for 1 hour at 250°C, for 1 hour at 350°C and for 3 hours at 475°C. In the last place, it was treated for 2 hours at 475°C in the mixed current of He and $H_2$.

By these procedures, Ru-carried La, Ca-Y-type Zeolite catalyst containing 1 wt.% as Ru was obtained.

Adamantane synthesis using this catalyst was carried out in the same manner as described in Example 12 and it was found that conversion rate of TMN, selectivity of AdH and yield of AdH were 99.0%, 23.9% and 23.7% respectively.

EXAMPLE 31

To 50 g of La, Ca-Y-type Zeolite powder, which was prepared in the manner as described in Example 3, 129,2 ml of Rh-solution containing 0.1292 g (i.e. 1 g/l) of $RhCl_3.3H_2O$ (Rh ion $3.798 \times 10^{-6}$ mol/ml) was poured and they were fully mixed at room temperature. Subsequently, the mixture was impregnated, evaporated and dried with rotary evaporator.

Obtained powder was placed in a ceramic board and heated in the current of He 50 cc/min., then calcined for 1 hour at 250°C, for 1 hour at 350°C and for 3 hours at 475°C. In the last place, it was treated for 2 hours at 475°C in the mixed current of He and $H_2$.

Thus obtained catalyst is Rh-carried La, Ca-Y-type Zeolite catalyst containing 1 wt.% as Rh.

Adamantane synthesis using this catalyst was carried out in the same manner as described in Example 12 and it was found that conversion rate of TMN, selectively of AdH and yield of AdH were 97.2%, 21.1% and 20.5% respectively.

What is claimed is:

1. A process for producing adamantane compounds which comprises isomerizing a tricyclic saturated hydrocarbon having 10 to 14 carbon atoms at from about 150°C to 300°C temperature in the presence of an X- or Y-type zeolite catalyst subjected to ion exchange with at least one metal ion selected from the group consisting of ions of rare earth metals, ions of calcium and ions of magnesium.

2. Process according to claim 1, wherein said tricyclic saturated hydrocarbon having 10 to 14 carbon atoms is a compound selected from endo-trimethylene norbornane, perhydroacenaphthene, perhydrofluolene, perhydrophenarene, 1,2-cyclo-pentanoperhydronaphthalin, perhydroanthracene, perhydrophenanthrene and 9-methylperhydroanthracene.

3. Process according to claim 2, wherein said isomerization reaction is carried out in the presence of hydrogen gas.

4. Process according to claim 2, wherein said isomerization reaction is carried out in the presence of $H_2$—HCl mixed gas.

5. Process according to claim 1, wherein said isomerization reaction is carried out in the presence of hydrogen gas.

6. Process according to claim 1, wherein said isomerization reaction is carried out in the presence of $H_2$—HCl mixed gas.

7. A process for producing adamantane compounds which comprises isomerizing a tricyclic saturated hydrocarbon having 10 to 14 carbon atoms at from about 150°C to 300°C temperature in the presence of an X- or Y-type zeolite catalyst subjected to ion exchange with at least one metal ion selected from the group consisting of ions of rare earth metals, ions of calcium, ions of magnesium and further being loaded with 1 to 4 metals selected from the group consisting of germanium, platinum, rhenium, nickel, cobalt, copper, iron, ruthenium and rhodium.

8. Process according to claim 7, wherein said tricyclic saturated hydrocarbon having 10 to 14 carbon atoms is a compound selected from endo-trimethylene norbornane, perhydroacenaphthene, perhydrofluolene, perhydrophenarene, 1,2-cyclo-pentanoperhydronaphthalin, perhydroanthracene, perhydrophenanthrene and 9-methylperhydroanthracene.

9. Process according to claim 8, wherein said isomerization reaction is carried out in the presence of hydrogen gas.

10. Process according to claim 8, wherein said isomerization reaction is carried out in the presence of $H_2$—HCl mixed gas.

11. Process according to claim 7, wherein said isomerization reaction is carried out in the presence of hydrogen gas.

12. Process according to claim 7, wherein said isomerization reaction is carried out in the presence of $H_2$—HCl mixed gas.

* * * * *